US011540923B2

(12) United States Patent
Carrasco et al.

(10) Patent No.: US 11,540,923 B2
(45) Date of Patent: Jan. 3, 2023

(54) CERAMIC ACETABULAR CUP (71) Applicant: MATORTHO LIMITED, Leatherhead (GB)

(72) Inventors: Carolina Avila Carrasco, Leatherhead (GB); Simon Collins, Tetbury (GB); Andrew Clive Taylor, Chichester (GB); Michael Antony Tuke, Guildford (GB)

(73) Assignee: MATORTHO LIMITED, Leatherhead (GB)

( * ) Notice: Subject to any disclaimer, the term of this patent is extended or adjusted under 35 U.S.C. 154(b) by 0 days.

(21) Appl. No.: 16/610,324

(22) PCT Filed: May 8, 2018

(86) PCT No.: PCT/GB2018/051227
§ 371 (c)(1),
(2) Date: Nov. 1, 2019

(87) PCT Pub. No.: WO2018/206931
PCT Pub. Date: Nov. 15, 2018

(65) Prior Publication Data
US 2020/0085582 A1    Mar. 19, 2020

(30) Foreign Application Priority Data
May 9, 2017    (GB) ..................................... 1707434

(51) Int. Cl.
*A61F 2/34*      (2006.01)
*A61F 2/30*      (2006.01)

(52) U.S. Cl.
CPC ........ *A61F 2/34* (2013.01); *A61F 2002/3093* (2013.01); *A61F 2002/30245* (2013.01);
(Continued)

(58) Field of Classification Search
CPC .............. A61F 2/34; A61F 2002/30324; A61F 2002/3446; A61F 2002/3453; A61F 2002/3459; A61F 2002/3462; A61F 2002/3466; A61F 2002/3429; A61F 2002/3495
See application file for complete search history.

(56) References Cited

U.S. PATENT DOCUMENTS 4,123,806 A * 11/1978 Amstutz ................... A61F 2/32
                                                   623/22.39
4,704,127 A    11/1987 Averill
(Continued)

FOREIGN PATENT DOCUMENTS

DE    9402941    6/1994
EP    1025815    8/2000
(Continued)

OTHER PUBLICATIONS

GB1707434.5—Search Report under Section 17, dated Sep. 14, 2017.
(Continued)

*Primary Examiner* — Brian A Dukert
(74) *Attorney, Agent, or Firm* — Nyemaster Goode, P.C.

(57) ABSTRACT

A ceramic acetabular cup devoid of a separate liner comprises a part-spherical inner articulating surface and an outer surface. An inner radius at or adjacent to a rim of the cup extends to or adjacent to a surface edge of the inner articulating surface. An inner radius of the inner articulating surface defines an active arc, and an uppermost portion of the rim defines an offset datum plane. An offset is provided between an equatorial centre of the inner articulating surface and the offset datum plane. The active arc extends in a range from around 150 degrees to less than 180 degrees, and a distance between the inner articulating surface and outer surface on a straight line from the said equatorial centre and passing through the surface edge is equal to or less than 4 mm.

15 Claims, 5 Drawing Sheets

(52) U.S. Cl.
CPC ............... *A61F 2002/30324* (2013.01); *A61F 2002/3446* (2013.01); *A61F 2002/3462* (2013.01); *A61F 2002/3466* (2013.01); *A61F 2310/00179* (2013.01); *A61F 2310/00407* (2013.01)

(56) References Cited

U.S. PATENT DOCUMENTS

| | | | | |
|---|---|---|---|---|
| 8,372,155 | B2* | 2/2013 | Tuke | B23P 11/02 |
| | | | | 623/22.32 |
| 8,388,887 | B2 | 3/2013 | Gupta | |
| 8,506,644 | B1 | 8/2013 | Ho Ba Tho | |
| 9,381,096 | B2* | 7/2016 | Davenport | A61F 2/34 |
| 9,649,194 | B2* | 5/2017 | Forsell | A61F 2/3609 |
| 2004/0186586 | A1 | 9/2004 | Seyer | |
| 2011/0251698 | A1 | 10/2011 | Gupta et al. | |
| 2014/0343682 | A1* | 11/2014 | Mangan | A61F 2/34 |
| | | | | 623/22.24 |
| 2016/0296289 | A1* | 10/2016 | Choudhury | G05B 15/02 |

FOREIGN PATENT DOCUMENTS

| | | |
|---|---|---|
| EP | 2174621 | 4/2010 |
| EP | 2174621 | 7/2013 |
| EP | 2990013 | 6/2017 |
| FR | 2877563 | 11/2007 |
| GB | 2529203 A | 2/2016 |
| GB | 2529203 B | 9/2016 |

OTHER PUBLICATIONS

EP1025815A1—English Translation.
DE9402941U1—English Translation.
EP2990013A1—English Translation.
GB1718591.9—Search Report under Section 17, and Combined Search and Examination Report under Sections 17 & 83(3), dated Dec. 20, 2017.
GB1718591.9—Examination Report under Section 18(3), dated Apr. 27, 2018.
GB1718591.9—Examination Report under Section 18(3), dated May 9, 2018.
GB1719834.2—Search Report under Section 17, dated Dec. 20, 2017.
PCT/GB2018/051227—International Search Report, dated Jan. 3, 2019.
FR2877563A1—English Translation.
WO2016102976A1—Publication of PCT/GB2015/054161, Matortho Ltd, Jun. 30, 2016.
Dec. 17, 2020 Examination Report for EP 18786379.0.
Oct. 21, 2021 Examination Report.

* cited by examiner

CERAMIC ACETABULAR CUP

The present invention relates to a ceramic acetabular cup which is devoid of a separate liner and which thus utilises a single shell forming an exterior bone-interfacing surface and an inner articulating surface for receiving a prosthetic femoral head. More particularly, the invention relates to such a cup which is thin walled, and to an acetabular cup system having a plurality of such cups which are geometrically different.

For total hip replacement operations, two constant requirements are sought after. The larger the diameter, the less likelihood of hip dislocation, particularly but not necessarily exclusively in younger and more active patients. However, it is also important to remove as little bone from the implant area as possible to allow for a future revision, if required, along with aiming to preserve the most natural biokinetic physiology of the patient.

Two part acetabular cup's have long been used in the field to enable a secure fit whilst retaining suitable strength. However, such two part cups having an outer shell and engagable inner liner still result in an overall wall thickness which can be too thick and consequently this restricts a femoral head size that can be utilised.

Furthermore, providing reliable bone fixation solely with a ceramic to bone interface has been heretofore a barrier to providing a ceramic only implant.

It is also a requirement to provide a radius at an inner edge of the rim of the cup to minimise edge loading effects and 'stripe-wear' that can cause early implant failure. However, any removal of material at the rim potentially causes weakness.

The present invention therefore seeks to provide a solution to these problems, thereby allowing a thin-walled ceramic cup to be achieved whilst maintaining sufficient operational strength, improved bone fixation and long term integrity.

According to a first aspect of the invention a ceramic acetabular cup devoid of a separate liner and comprising: a part-spherical inner articulating surface for non-captively receiving a femoral head; an outer surface for enabling direct to bone fixation; an inner radius at or adjacent to a rim of the cup and extending to or adjacent to a surface edge of the inner articulating surface to prevent or reduce undesirable effects of impingement of an associated femoral head and/or neck; an inner radius of the inner articulating surface defining an active arc over which an in use femoral head can articulate; an uppermost portion of the rim defining an offset datum plane; an offset between an equatorial centre of the inner articulating surface and the offset datum plane being in a range of around 1 mm towards a pole of the inner articulating surface and around 3.5 mm away from the said pole; the active arc extending in a range from around 150 degrees to, and preferably to less than, 180 degrees; and a distance between the inner articulating surface and outer surface on a straight line from the said equatorial centre and passing through the surface edge being equal to or less than 4 mm.

Preferably, said equatorial centre of the inner articulating surface may be offset from a geometric centre of the outer surface.

Preferably, the outer surface may be at least in part part-spherical.

Preferably, the outer surface may be non-spherical.

Preferably, the outer surface may include a straight-walled or substantially straight-walled portion in a polar direction.

Preferably, the straight-walled portion may define one of a cylindrical wall or a frusto-conical wall.

Preferably, the straight-walled portion may extend from or adjacent to the rim.

Preferably, a wall thickness between the inner articulating surface and the outer surface may be non-uniform.

Preferably, the wall thickness may increase towards the said pole.

Preferably, the outer surface may be porous for improving direct to bone fixation.

Preferably, the outer surface may support one or more layers of a bio-compatible coating.

Preferably, the said coating may be stepped at or adjacent to the rim.

Preferably, the outer surface may flare at or adjacent to the rim.

Preferably, a wall thickness between the inner articulating surface and the outer surface may stepwise fractionally decrease as the offset increases in a positive direction away from the pole.

Preferably, a radial cross-section of the rim may be asymmetric.

Preferably, the rim may include an inner radiused edge and an outer radiused edge, an arcuate extent of each said edge being different to accommodate different offsets, active arcs and outer surface coatings.

Preferably, the rim may include a flat between the inner radiused edge and the outer radiused edge, the flat defining the offset datum plane.

Preferably, the inner articulating surface and outer surface to define said straight line may be curved and flat, respectively, in a polar direction.

According to a second aspect of the invention a ceramic acetabular cup devoid of a separate liner and comprising a distance between an inner articulating surface and an outer surface on a straight line from an equatorial centre of the inner articulating surface and passing through a surface edge of the inner articulating surface at a transition to a rim, which is equal to or less than 4 mm.

According to a third aspect of the invention an acetabular cup system comprising a plurality of geometrically different ceramic acetabular cups according to the first and/or second aspects of the invention and which are devoid of liners, each said cup having a distance, which is between an inner articulating surface and an outer surface on a straight line from a equatorial centre of the inner articulating surface and passing through a surface edge of the inner articulating surface at a transition to a rim, which is equal to or less than 4 mm.

According to a fourth aspect of the invention, there is provided a method of setting a wall-thickness distance at or adjacent to a rim of a ceramic acetabular cup in accordance with the first aspect of the invention, the method comprising the steps of: a] determining an offset of an equatorial centre of a part-spherical inner articulating surface; b] determining an active arc of the part-spherical inner articulating surface; c] determining a required radiused inner edge of the rim; and d] a straight line between the inner and outer surfaces and collinear with a radial maximum extent of the active arc intersecting an edge of the radiused inner edge of the rim defining a required wall-thickness distance which is less than or equal to 4 mm.

The invention will now be more particularly described, by way of example only, with reference to the accompanying drawings, in which.

Figure 1:
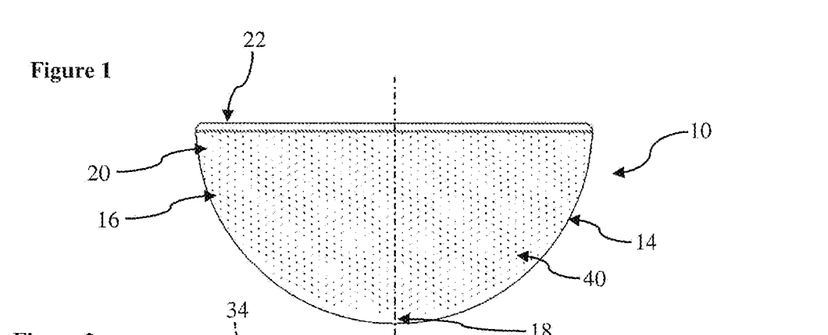
FIG. 1 shows an exterior elevational view of a first embodiment of a ceramic acetabular cup, in accordance with the first and second aspects of the invention and forming part of the third aspect of the invention.
Figures 2, 3:
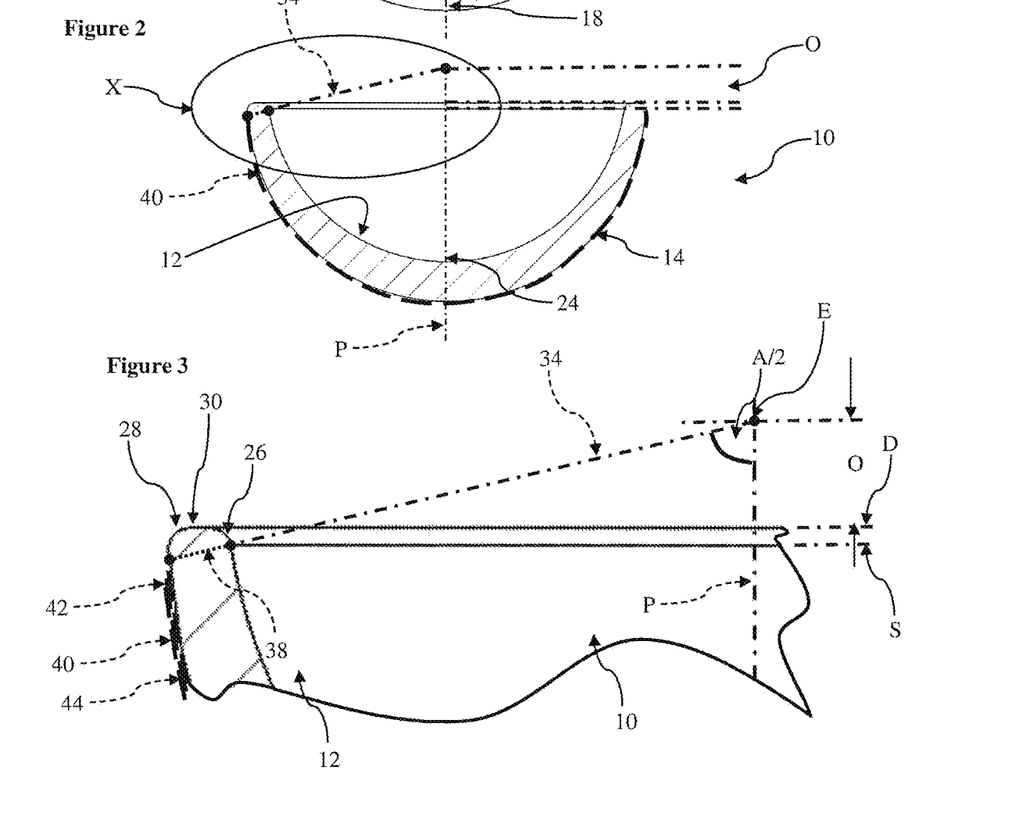
FIG. 2 is a polar cross-sectional view of the ceramic acetabular cup, shown in FIG. 1 and indicating a positive offset of an active arc of an inner articulating surface.
FIG. 3 is an enlarged portion of part 'X' referenced in FIG. 2, showing a portion of a rim and a polar axis of the ceramic acetabular cup.

Referring firstly to FIGS. 1 to 3 of the drawings, there is shown a first embodiment of a ceramic acetabular cup 10 which is dimensioned to fit a prepared natural acetabulum of a patient. The cup 10 is formed as one-piece from ceramic, and as such is devoid of a separate inner liner. The cup 10 comprises a part-spherical inner articulating surface 12 for non-captively receiving a ball of a femoral head of a femur and/or implant, and a bone-interfacing outer surface 14 which enables direct to bone fixation.

In this embodiment, the outer surface 14 includes a part-spherical portion 16 which extends from an outer polar region 18 of the cup 10, and a frusto-conical portion 20 which extends from the termination of the part-spherical portion 16 to a rim 22 of the cup 10. Such a multi-geometric outer surface 14 aids manufacture, implantation and/or fixation. As will be understood from the subsequent embodiments, other different geometric outer surface profiles may be utilised. As such, in this embodiment, the frusto-conical portion 20 may be dispensed with or may extend a different distance towards or away from the polar region 18.

Where present, the frusto-conical portion herein and throughout may have a cone angle which is greater than zero to or to around preferably 15 degrees, dependent on necessity. An axial length of a wall of the frusto-conical portion may be between 2 mm and 15 mm, or as required.

The inner bearing articulating surface 12 is preferably entirely part-spherical from and including an inner polar region 24 to the rim 22. The articulating surface 12 is smoothly continuous and thus unbroken and unapertured.

At least a majority of a wall thickness between the inner articulating surface 12 and the outer surface 14 typically increases in thickness towards the polar axis P. However, exterior formations may be provided on, at or in the outer surface 14, such as one or more flared portions and/or one or more recessed portions. Such formations may be beneficial for assisting introduction and/or removal of the cup 10 during surgery and enhancing primary press-fit fixation.

The rim 22 of the cup 10 includes a radiused inner edge 26 which extends in this case to contiguously meet the inner articulating surface 12. The radius at the inner edge 26 assists in limiting the effects in use of dislocation of the femoral head, and/or impact wear or damage on the head or neck of the femoral component or vice versa.

In the present embodiment, the rim 22 also includes a radiused outer edge 28.

The rim 22 preferably has an asymmetric radial cross-section.

The radiuses of both the inner and outer edges 26, 28 are preferably uniformly constant and uninterrupted around the circumference of the rim 22. An arcuate extent of each said edge is preferably different to accommodate different offsets, active arcs and outer surface coatings.

The rim 22 also includes a flat 30 which is interposed between the inner and outer radiuses. However, the flat 30 may be dispensed with, for example, in the case where one or both radiused inner and outer edges 26, 28 extend to meet the other. As such, the radiuses may be the same or different, dependent on necessity.

To optimise the dimension of the acetabular cup 10 to accommodate a greatest number of femoral heads with a minimum wall thickness to thus reduce an amount of bone to be removed whilst still enabling sufficient cup strength, a required active arc A, half of which A/2 is shown in the drawings for clarity, over which the inner bearing articulating surface 12 extends is determined along with a required radius of the inner edge 26 of the rim 22 to minimise or optimise a determined impingement of the femoral head or neck during use. This latter criterion may be determined entirely or at least in part by data relating to a lifestyle of the patient and thus a typical range of motion required at the hip.

To therefore determine an offset O of an equatorial centre E of the inner articulating surface 12 from the rim 22, an offset datum plane D which in this case is perpendicular to a polar axis P is defined by an uppermost or outermost portion of the rim 22 in a direction away from the pole along the polar axis P, which in this case is at the flat 30.

The active arc A is a radius of the inner articulating surface 12 with the radial equatorial centre E being, in this example, on the polar axis P. The equatorial centre E may thus be offset in a positive direction away from the pole 24 of the inner articulating surface 12 from the offset datum plane D; may be offset in a negative direction towards the pole 24 of the inner articulating surface 12 from the offset datum plane D, see FIG. 15; or may be coincident with the offset datum plane D and consequently applying a 'zero' offset O with respect to the offset datum plane D. In this way, the, preferably patient-specific, selected, determined or preferred radiused inner edge 26 is accommodated whilst maximising an opening to the inner articulating surface 12 to accept insertion of a required femoral head.

To maintain an optimum or preferred structural integrity of the acetabular cup 10 with a minimum or optimised wall thickness at or adjacent to an opening of a patient's acetabulum, a radial extent of the inner articulating surface 12 at the maximum angular extents 34 of the active arc A, typically therefore being at the interface, edge or boundary S between the rim 22 and the inner bearing articulating surface 12, is extended, projected or extrapolated a wall-thickness distance 38 to meet the outer surface 14 of the cup 10. The wall-thickness distance 38 is equal to or less than 4 millimetres, and is preferably between 3 mm and 4 mm.

The wall-thickness distance 38 is thus taken on a straight line which is collinear with the radial maximum angular extent 34 of the active arc A at the perimeter surface edge S of the inner articulating surface 12. The inner articulating surface 12 and outer surface 14 to define said straight line are preferably curved and flat, respectively, in a polar direction.

By thus determining a required radius of the inner rim edge 26, required opening of the inner articulating surface 12, and a required active arc A of the inner articulating surface 12 for a specific acetabular cup 10, the necessary offset O can be determined. With the offset O known, an optimum minimum wall thickness at or adjacent to the rim 22 can be determined. The acetabular cup 10 can thus be formed to meet patient specific criteria whilst minimising a wall thickness and without impacting in use structural integrity.

With the relative geometries of the outer surface 14, the inner articulating surface 12, and the rim 22 determined to achieve optimal rigidity and longevity with minimum bone removal, a bone-fixation coating may be applied to the outer surface 14.

To this end, although the ceramic outer surface 14 in this embodiment is smooth, it may be roughened to promote adhesion of a coating 40, and this may be achieved by rough-grinding, particle blasting, and/or etching, for example. Vapour deposition, for example, by sputtering of pulverised coating material under high vacuum can be considered, and such a coating 40 can be built up in layers 42. Spraying, for example plasma spraying, may also be considered, and again multiple layers may be utilised.

It is preferred that any bone-fixation coating 40 is between 50 microns to 500 microns, and preferably extends over the entirety or substantially entire outer surface 14.

Biocompatible metals and metal alloys are suitable for coating purposes. The thermal and mechanical properties make titanium-based alloys, for example $TiAl_6V_4$ and $TiAl_6Nb_7$, particularly advantageous.

In order to facilitate and accelerate ingrowth of the implant into the bone, the coating 40 can be provided with a bioactive covering 44. A covering 44 that is known for these purposes is, for example, hydroxyapatite.

Where multiple layers of the biocompatible bone-fixation coating 40 is required, it may be preferred to feather or step the perimeter edge of the coating 40 at or adjacent to the, preferably radiused, outer rim edge 28. This enables the minimum determined wall-thickness distance 38, explained above, to be maintained or substantially maintained.

It may be feasible simply to roughen the outer surface 14 of the acetabular cup 10, and thus dispense with the bone-fixation coating 40.

It may also be feasible to provide a liquid or flowable solution of liquid bone-growth promotion material separately of the acetabular cup 10. For example, the flowable bone-growth promotion material may be applied to a patient's acetabulum intraoperatively, coating the opening of the acetabulum, before the coated or uncoated acetabular cup is inserted. This may have the advantage in that the flowable bone-growth promotion material can be accommodated in more bone irregularities, thus allowing an improved fixation interface with the outer surface 14 of the acetabular cup 10 once inserted. Such an approach could be utilised in one-piece direct fixation acetabular cups, and outer shells of multiple part acetabular cups.

Consequently, the flowable bone-growth promotion material would preferably rapidly cure or set following seating of the acetabular cup.

Figure 4:
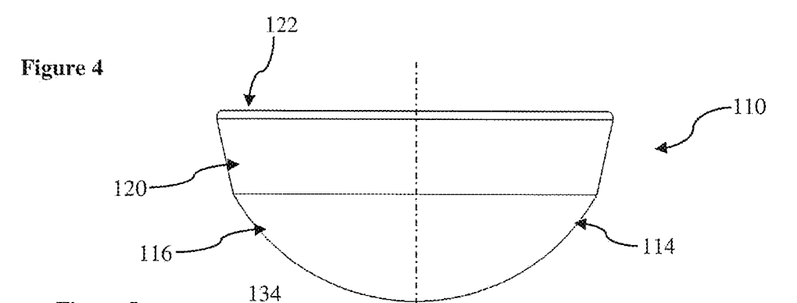
FIGS. 4 to 6 are similar views to those of FIGS. 1 to 3, respectively, of a second embodiment of a ceramic acetabular cup, in accordance with the first and second aspects of the invention and forming part of the third aspect of the invention.
Figure 5:
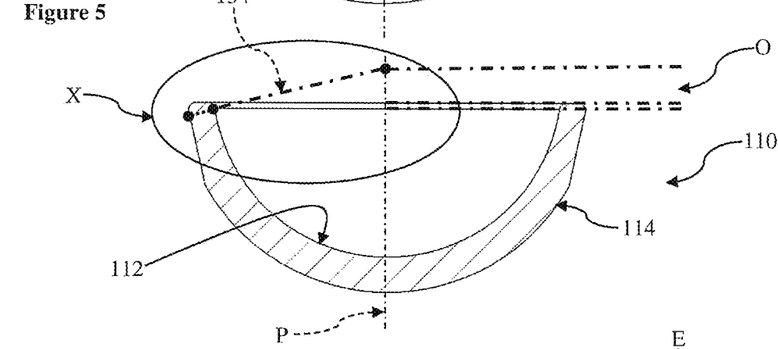
Figure 6:
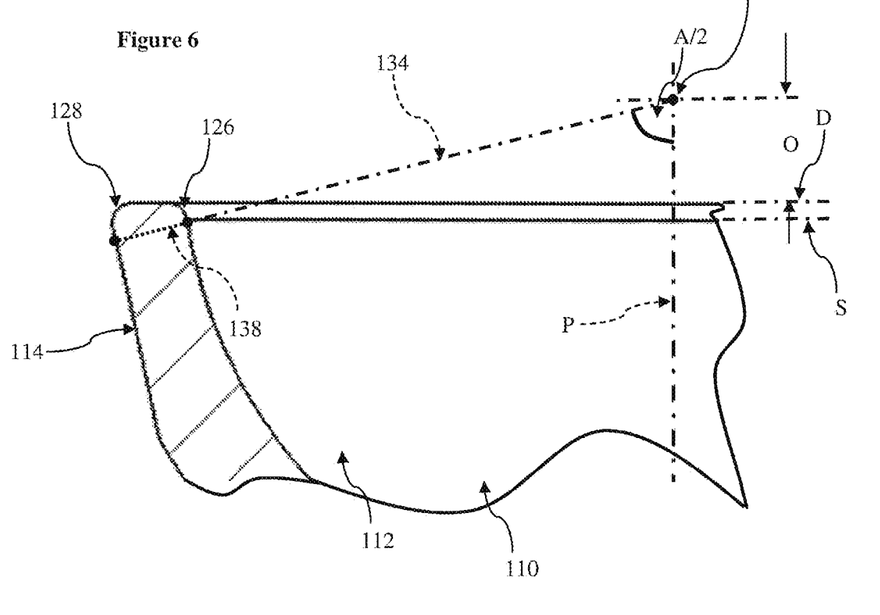

Referring now to FIGS. 4 to 6 of the drawings, a second embodiment of the ceramic acetabular cup is similar to that of the first embodiment. Similar references are therefore used for parts which are similar to those of the first embodiment, with one hundred added. Further detailed description is omitted for brevity, and the optional biocompatible coating on the outer surface is omitted for clarity.

This ceramic acetabular cup 110 is again intended for direct bone fixation and is without a separate inner liner. As such, as in the first embodiment, the acetabular cup 110 comprises a part-spherical inner articulating surface 112 for non-captively receiving a femoral head, an outer surface 114 for enabling direct to bone fixation, and the rim 122 with at least an inner radius interposed between the inner and outer surfaces 112, 114.

The outer surface 114 in this embodiment has a part-spherical portion 116 which extends from an exterior polar region, and, similarly to the first embodiment, a frusto-conical portion 120 which extends contiguously from the part-spherical portion 116 to the rim 122.

As in the first embodiment, the rim 122 also includes a radiused outer edge 128, but this may be dispensed with, and/or may have a same radius or different radius to that of the radiused inner edge 126.

The uppermost portion of the rim 122 again defines the offset datum plane D which is at right angles to the polar axis P, and a radius of the inner bearing articulating surface 112 defines the active arc A which extends to the start of the radiused inner edge 126 of the rim 122 in a direction away from the inner polar region 124.

The active arc A again extends from around 150 degrees to preferably less than 180 degrees. With the radiused inner edge 126 of the rim 122 determined, and the required active arc A known, an offset O from the offset datum plane D can be determined, and a radial line at the extents 134 of the active arc A can be extended linearly to meet the outer surface 114, allowing an optimum wall-thickness distance 138 along this line to be set at 4 mm or less to achieve a suitable balance between robustness of the cup 110 along with inner and outer surface major dimensions at or adjacent to the rim 122 and perpendicular to the polar axis P.

If required, the bone-fixation coating may be applied to the entire or only part of the outer surface 114, as described above.

Figure 7:
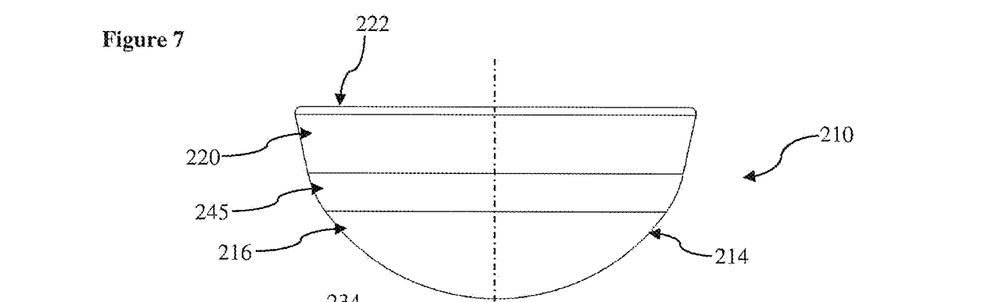
FIGS. 7 to 9 are again similar views to those of FIGS. 1 to 3, respectively, of a third embodiment of a ceramic acetabular cup, in accordance with the first and second aspects of the invention and forming part of the third aspect of the invention.
Figure 8:
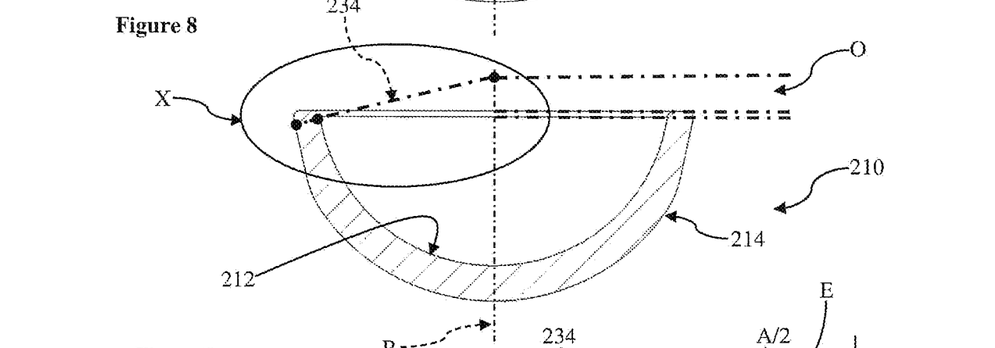
Figure 9:
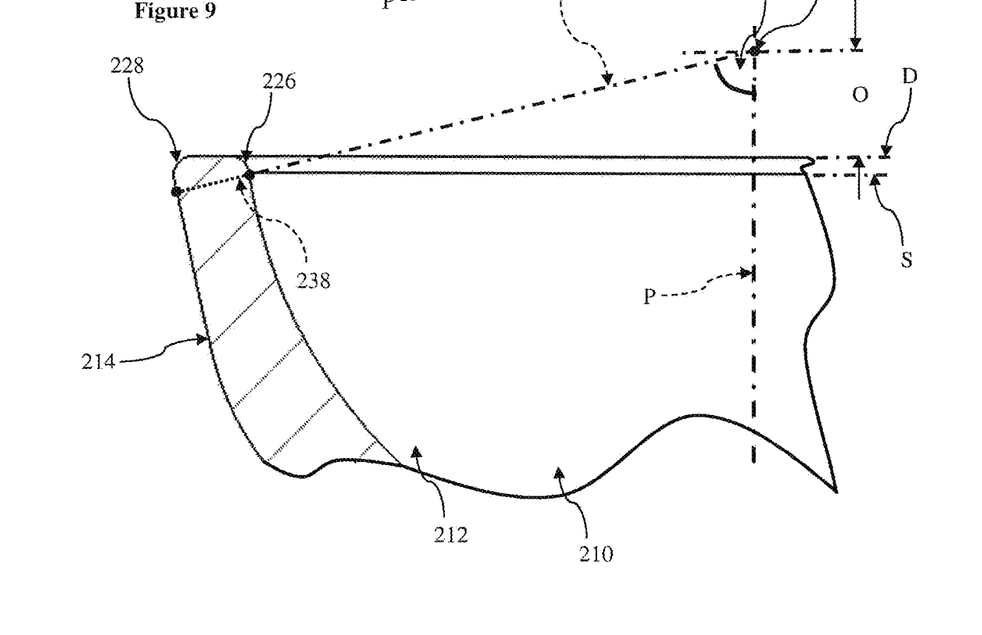

Referring now to FIGS. 7 to 9 of the drawings, a third embodiment of the ceramic acetabular cup is similar to that of the first and second embodiments. Similar references are therefore used for parts which are similar to those of the first embodiment, with two hundred added. Further detailed description is omitted for brevity, and the optional biocompatible coating on the outer surface is omitted for clarity.

As above, this ceramic acetabular cup 210 is again intended for direct bone fixation and is, without a separate inner liner. As such, the acetabular cup 210 comprises a part-spherical inner articulating surface 212 for non-captively receiving a femoral head, an outer surface 214 for enabling direct to bone fixation, and the rim 222 with at least an inner radius interposed between the inner and outer surfaces 212, 214.

The outer surface 214 in this embodiment has a part-spherical portion 216 with a first radius and which extends from an exterior polar region, a part-spheroidal portion 245 or arcuate wall portion which extends contiguously from the part-spherical portion 216, and a frusto-conical portion 220 which extends contiguously from the part-spheroidal portion 245 to the rim 222. The part-spherical portion 216 and the part-spheroidal portion 245 have different radii, and the part-spheroidal portion 245 may have an irregular or non-uniform radius in a polar direction of the acetabular cup 210.

As in the first embodiment, the rim 222 also includes a radiused outer edge 228, but this may be dispensed with, and/or may have a same radius or different radius to that of the radiused inner edge 226.

The offset datum plane D is defined by the rim 222, which as before is preferably perpendicular to the polar axis P. The inner articulating surface 212 provides the active arc A, preferably being around 150 degrees to less than 180 degrees and over which a femoral head can articulate. The active arc A extends to a lowermost perimeter edge of the radiused inner rim 222, and with a required offset O being known to set a depth of the cup 210, a radius of the active arc A at the extents 234 of the active surface 212 can be linearly extended to meet the outer surface 214, thereby allowing the wall-thickness distance 238 on this line to be set at approximately 4 mm or less.

Figure 10:
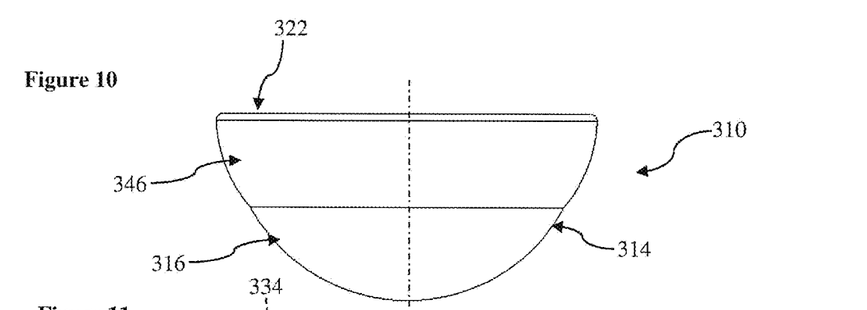
FIGS. 10 to 12 are yet again similar views to those of FIGS. 1 to 3, respectively, of a fourth embodiment of a ceramic acetabular cup, in accordance with the first and second aspects of the invention and forming part of the third aspect of the invention.
Figures 11, 12:
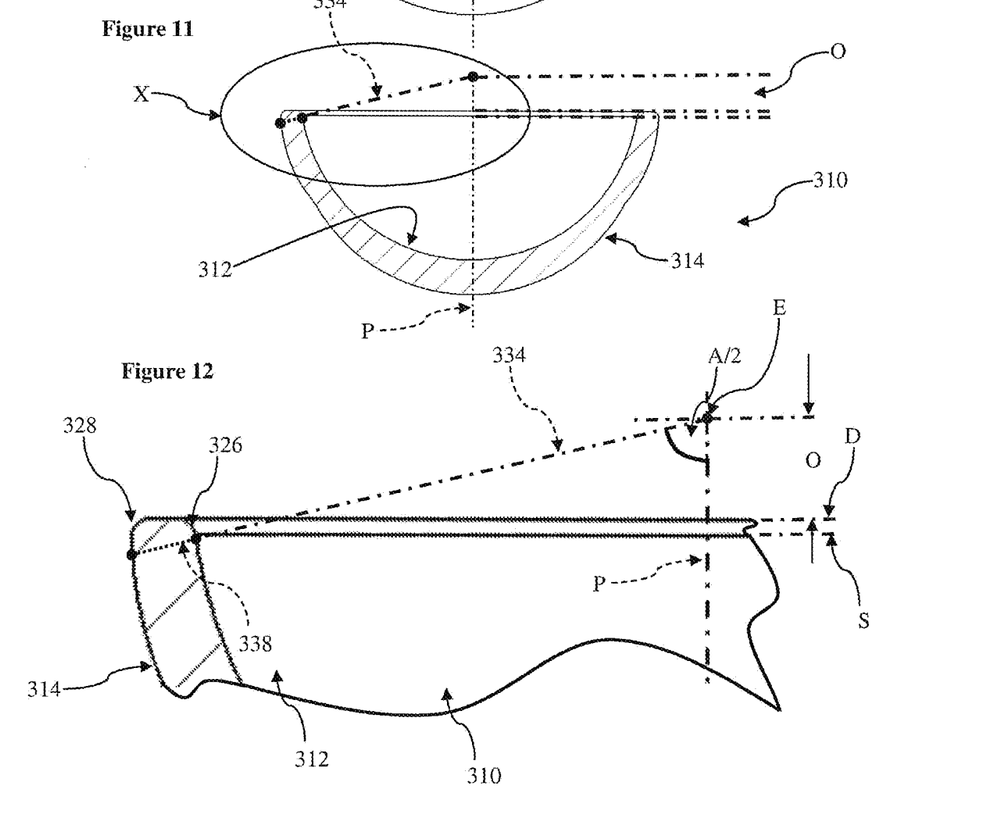

Referring now to FIGS. 10 to 12 of the drawings, a fourth embodiment of the ceramic acetabular cup is similar to that of the first to third embodiments. Similar references are therefore used for parts which are similar to those of the first embodiment, with three hundred added. Further detailed description is omitted for brevity, and the optional biocompatible coating on the outer surface is omitted for clarity.

As above, this ceramic acetabular cup 310 is again intended for direct bone fixation and is without a separate inner liner. The acetabular cup 310 thus comprises a part-spherical inner articulating surface 312 for non-captively receiving a femoral head, an outer surface 314 for enabling direct to bone fixation, and the rim 322 with at least an inner radius interposed between the inner and outer surfaces 312, 314.

The outer surface 314 in this embodiment has a first part-spherical portion 316 with a first radius and which extends from an exterior polar region, and a second part-spherical portion 346 or arcuate wall portion which extends contiguously from the first part-spherical portion 316 to meet the rim 322. The first and second part-spherical portions 316, 346 have different radii. In all cases, although the outer surface 314 utilises one or more part-spherical portions, curved or planar surfaces may be used, and these surfaces may have common dimensions and/or may be irregular. Protrusions and recesses may also be utilised where necessary.

As in the first embodiment, the rim 322 includes a radiused outer edge 328, but this may be dispensed with, and/or may have a same radius or different radius to that of the radiused inner edge 326.

The offset datum plane D is again preferably defined by the rim 322, which as before is preferably although not necessarily exclusively perpendicular to the polar axis P. The inner articulating surface 312 provides the active arc A, preferably being around 150 degrees to less than 180 degrees and over which a femoral head can articulate. The active arc A extends to a lowermost perimeter edge S of the radiused inner edge 326 of the rim 322, and with a required offset O being known to set a depth of the cup 310, a radius of the active arc A at the extents 334 of the active surface 312 can be linearly extended to meet the outer surface 314, thereby allowing a wall-thickness distance 338 on this line to be set at approximately 4 mm or less.

Figure 13:
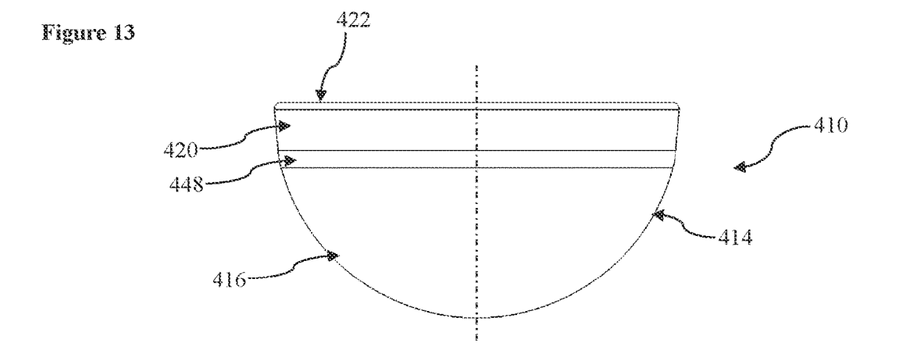
FIGS. 13 to 15 are similar views to those of FIGS. 1 to 3, respectively, of a second embodiment of a ceramic acetabular cup, in accordance with the first and second aspects of the invention and forming part of the third aspect of the invention, and in this case indicating a negative offset of an active arc of an inner articulating surface.
Figure 14:
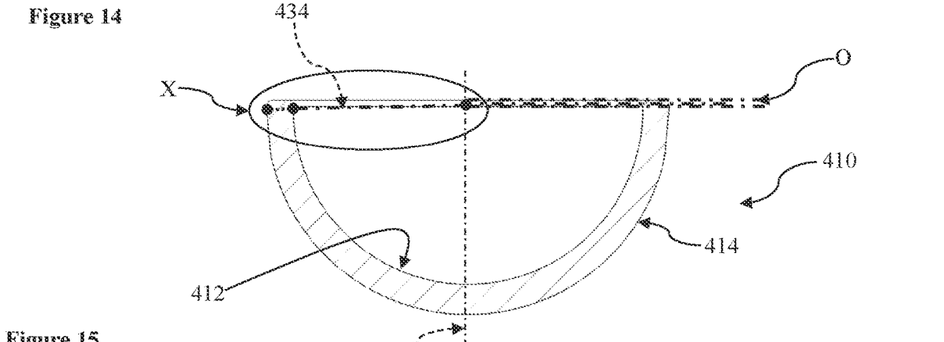
Figure 15:
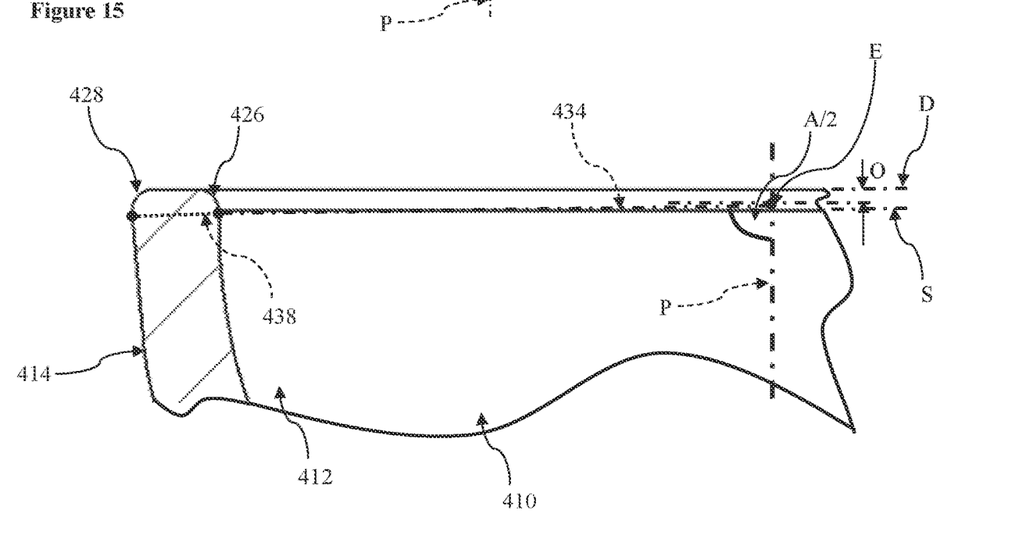

Referring now to FIGS. 13 to 15 of the drawings, a fifth embodiment of the ceramic acetabular cup is similar to that of the first to fourth embodiments. Similar references are therefore used for parts which are similar to those of the first embodiment, with four hundred added. Further detailed description is omitted for brevity, and the optional biocompatible coating on the outer surface is omitted for clarity.

As above, this ceramic acetabular cup 410 is again intended for direct bone fixation and is without a separate inner liner. The acetabular cup 410 thus comprises a part-spherical inner articulating surface 412 for, preferably non-captively, receiving a femoral head, an outer surface 414 for enabling direct to bone fixation, and the rim 422 with at least an inner radius interposed between the inner and outer surfaces 412, 414.

Although non-captive is preferred, all the embodiments herein may have one or more features or elements which captively engage a femoral head. In this case, the active arc A may be greater than 180 degrees. It may also be feasible that the active arc A is 180 degrees.

The outer surface 414 in this embodiment has a part-spherical portion 416 with a first radius and which extends from an exterior polar region, a frusto-conical portion 420 which extends to meet the rim 422, and an intermediary wall portion 448 which transitions the part-spherical portion 416 to the frusto-conical portion 420.

As in the first embodiment, the rim 422 includes a radiused outer edge 428, but this may be dispensed with, and/or may have a same radius or different radius to that of the radiused inner edge 426.

The offset datum plane D is again preferably defined by the rim 422, which as before is preferably perpendicular to the polar axis P. The inner articulating surface 412 provides the active arc A of around 150 degrees to preferably less than 180 degrees and over which a femoral head can articulate. The active arc A extends to a lowermost perimeter edge S of the radiused inner edge 426 of the rim 422. In this case, the offset O is negative, being below the offset datum plane D in a direction towards the inner polar region of the inner articulating surface 412. The negative offset O may be up to 1 millimetre. This allows for a greater active arc A and thus also a greater opening to the inner articulating surface 412.

In any event, with the required offset O being known, a radius of the active arc A at the extents 434 of the active surface 412 can be linearly extended to meet the outer surface 414, thereby again allowing a wall-thickness distance 438 on this line to be set at approximately 4 mm or less to achieve an optimum or preferred wall thickness to robustness ratio.

An acetabular cup system can therefore also be provided which utilises a plurality of geometrically different said ceramic acetabular cups being devoid of liners. Examples of such acetabular cups are described above, but are not necessarily limited to such. By providing such a system, a surgeon can select a suitable cup for a patient in the knowledge that a common wall thickness criterion is being met and adhered to. This consequently enables more comparable data sets to be formed regarding performance and longevity of the associated acetabular cups involving different geometries.

It is thus possible to provide a direct-to-bone one-piece ceramic acetabular cup with a wall thickness which is determined based on an offset, active arc, and lateral extent of a radiused inner rim edge to achieve a 4 mm or less distance. Consequently, as a required depth of the inner bearing articulating surface increases, a linear dimension along a radial axis at the extents of the active arc between the inner and outer surfaces can remain constant or substantially constant. This thus allows a wall thickness to be stepwisely fractionally decreased as the offset increases in a positive direction away from the inner polar region. In this way, strength to accommodate larger femoral heads can be accommodated whilst still maintaining as thin a wall as possible.

The words 'comprises/comprising' and the words 'having/including' when used herein with reference to the present invention are used to specify the presence of stated features, integers, steps or components, but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The embodiments described above are provided by way of examples only, and various other modifications will be apparent to persons skilled in the field without departing from the scope of the invention as defined herein.

The invention claimed is:

1. A one-piece ceramic acetabular cup devoid of a separate liner and comprising:
   a part-spherical inner articulating surface to non-captively receive a femoral head;
   an outer surface to enable direct to bone fixation and to support one or more layers of bio-compatible coating;
   an inner radius at or adjacent to a rim of the cup and extending to or adjacent to a surface edge of the inner articulating surface to prevent or reduce undesirable effects of impingement of an associated femoral head and/or neck;
   the rim having an inner radiused edge, an outer radiused edge, and a flat therebetween;
   an inner radius of the inner articulating surface defining an active arc over which an in use femoral head can articulate;
   the flat being an uppermost portion of the rim defining an offset datum plane;
   an offset between an equatorial centre of the inner articulating surface and the offset datum plane being in a range of 1 mm towards a pole of the inner articulating surface and 3.5 mm away from the said pole;
   the active arc extending in a range from 150 degrees to less than 180 degrees; and
   a distance between the inner articulating surface and outer surface on a straight line from the said equatorial centre and passing through the surface edge being equal to or less than 4 mm;
   wherein a wall thickness between the inner articulating surface and the outer surface is non-uniform such that the wall thickness of the acetabular cup increases from the flat towards the pole to be thickest at the pole.

2. The one-piece ceramic acetabular cup as claimed in claim 1, wherein said equatorial centre of the inner articulating surface is offset from a geometric centre of the outer surface.

3. The one-piece ceramic acetabular cup as claimed in claim 1, wherein the outer surface is at least in part part-spherical or is non-spherical.

4. The one-piece ceramic acetabular cup as claimed in claim 1, wherein the outer surface includes a straight-walled or substantially straight-walled portion in a polar direction.

5. The one-piece ceramic acetabular cup as claimed in claim 4, wherein the straight-walled portion defines one of a cylindrical wall or a frusto-conical wall.

6. The one-piece ceramic acetabular cup as claimed in claim 4, wherein the straight-walled portion extends from or adjacent to the rim.

7. The one-piece ceramic acetabular cup as claimed in claim 1, wherein the outer surface is porous to improve direct to bone fixation.

8. The one-piece ceramic acetabular cup as claimed in claim 1, wherein the said coating is stepped at or adjacent to the rim.

9. The one-piece ceramic acetabular cup as claimed in claim 1, wherein the outer surface flares at or adjacent to the rim.

10. The one-piece ceramic acetabular cup as claimed in claim 1, wherein a wall thickness between the inner articulating surface and the outer surface stepwise fractionally decreases as the offset increases in a positive direction away from the pole.

11. The one-piece ceramic acetabular cup as claimed in claim 1, wherein a radial cross-section of the rim is asymmetric.

12. The one-piece ceramic acetabular cup as claimed in claim 1, wherein the inner articulating surface and outer surface to define said straight line are curved and flat, respectively, in a polar direction.

13. An acetabular cup system comprising a plurality of geometrically different one-piece ceramic acetabular cups as claimed in claim 1 and which are devoid of liners, each said cup having a distance, which is between an inner articulating surface and an outer surface on a straight line from a equatorial centre of the inner articulating surface and passing through a surface edge of the inner articulating surface at a transition to a rim, which is equal to or less than 4 mm.

14. The one-piece ceramic acetabular cup as claimed in claim 1, wherein the one or more layers of bio-compatible coating cover at least a portion of the outer surface.

15. The one-piece ceramic acetabular cup as claimed in claim 1, wherein the inner radiused edge and the outer radiused edge each have an arcuate portion, and the arcuate portion of the inner radiused edge is different than the arcuate portion of the outer radiused edge to accommodate different offsets, active arcs and outer surface coatings.

* * * * *